United States Patent [19]

Barney

[11] Patent Number: 5,422,067

[45] Date of Patent: Jun. 6, 1995

[54] INSTRUMENT CASSETTE AND METHOD FOR USING THE SAME

[76] Inventor: Everett A. Barney, 3409 E. 29th St., Vancouver, Wash. 98661

[21] Appl. No.: 945,162

[22] Filed: Sep. 15, 1992

[51] Int. Cl.6 .......................... A61L 2/02; A61L 2/16; A61B 19/02

[52] U.S. Cl. .................................... 422/20; 422/300; 206/369; 206/63.5

[58] Field of Search .............. 422/20, 297, 300, 292; 206/438, 63.5, 363, 369, 370; 220/323, 324; 24/460, 461, 462, 564, 454, 487, 563, 564; 248/500, 510

[56] References Cited

U.S. PATENT DOCUMENTS

| | | | |
|---|---|---|---|
| 3,285,409 | 11/1966 | Loran | 206/63.5 |
| 3,757,031 | 9/1973 | Izraeli | 24/459 X |
| 3,868,016 | 2/1975 | Szpur et al. | 206/63.5 X |
| 4,135,868 | 1/1979 | Schainholz | 206/438 X |
| 4,562,047 | 12/1985 | Sestak et al. | 422/300 |
| 4,854,475 | 8/1989 | Riihimaki et al. | 220/337 |
| 4,930,660 | 6/1990 | Porteous | 206/63.5 X |
| 4,959,199 | 9/1990 | Brewer | 422/300 |
| 5,215,726 | 6/1993 | Kudla et al. | 422/297 |
| 5,294,413 | 3/1994 | Riihimaki et al. | 206/370 X |
| 5,346,677 | 9/1994 | Risk | 422/297 |

FOREIGN PATENT DOCUMENTS

| | | |
|---|---|---|
| 621270 | 1/1981 | Switzerland . |
| 1350571 | 4/1974 | United Kingdom ............ 24/459 |

*Primary Examiner*—Robert J. Warden
*Assistant Examiner*—E. Leigh Dawson
*Attorney, Agent, or Firm*—Steinberg, Raskin & Davidson

[57] ABSTRACT

A cassette for holding instruments, such as medical and dental instruments, through cleaning, sterilization, storage and use cycles, comprises a tray member having a bottom wall and a pair of opposite side walls, at least two clamping members fixed to the bottom wall extending transversely between the side walls, and at least one clip member releasably securable to the tray side walls for overlying and clamping the instruments against the clamping members so as to remain exposed. A method for using the instrument cassette comprises placing the cassette containing the instruments in an ultrasonic cleaning device, preferably after hand-scrubbing the instruments which have been arranged and secured within the cassette, and then sterilizing the instruments in the cassette.

20 Claims, 3 Drawing Sheets

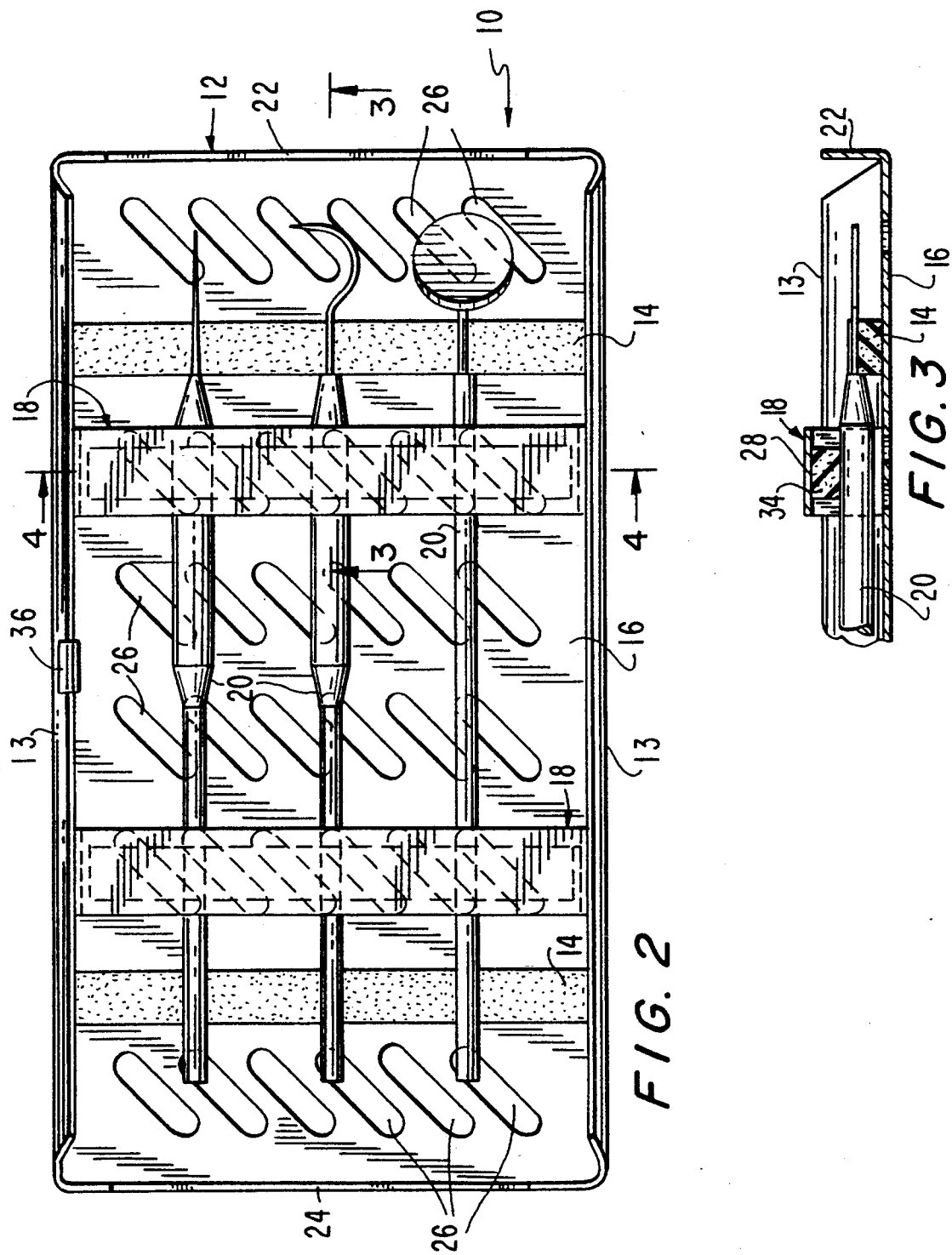

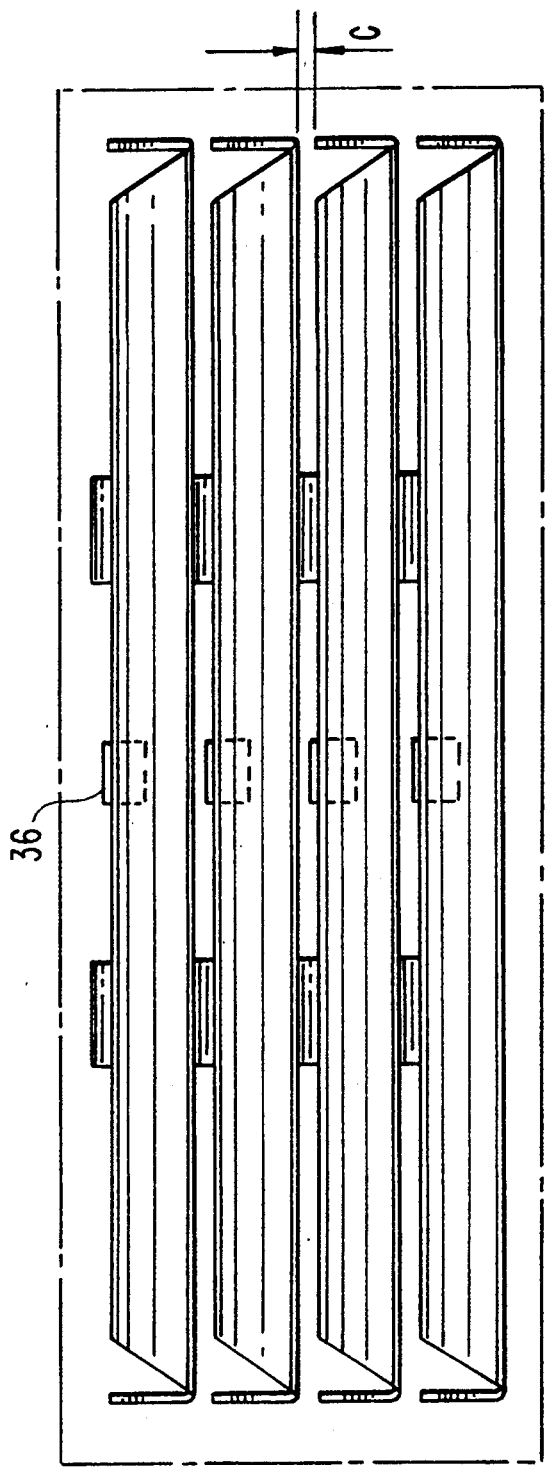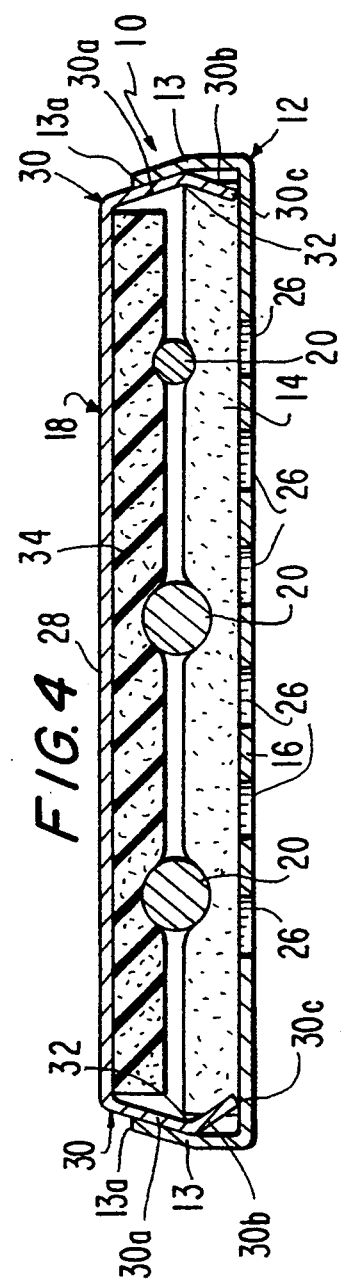

INSTRUMENT CASSETTE AND METHOD FOR USING THE SAME

BACKGROUND OF THE INVENTION

This invention relates to cassettes for holding instruments, such as medical and dental instruments, through cleaning, sterilization, storage and use cycles, as well as to methods for using such cassettes.

Attempts have been made in the past to provide cassettes for holding medical and dental instruments and the like while the instruments are being cleaned and sterilized. The sterilized instruments are kept within the cassette until they are ready to be used again, whereupon the cassette is placed at a convenient location for the practitioner who then is provided with the instrument directly from the cassette.

Such prior art cassettes generally include a lower tray member to which an upper cover member is hinged to form an openable and closable enclosure. Means for clamping the instruments between them, such as resilient rubber pads or cushions, are fixed within the lower tray and upper cover members. In use, instruments to be cleaned and sterilized are arranged on the lower clamping means in the lower tray member whereupon the cover member is pivoted to close the cassette so that the instruments are clamped between the upper and lower clamping means. The tray and cover members, which may be formed of metallic or plastic material, have patterns of holes formed in them to allow for an unimpeded fluid flow into and out from the interior of the cassette to facilitate proper ultrasonic cleaning and sterilization of the instruments.

There are several drawbacks in the construction and use of conventional instrument cassettes. A major objection is that they are relatively bulky in size so that only a very small number of the cassettes can be placed in ultrasonic cleaning machines and autoclaves at any one time. The hinged cover construction, as well as the construction of the upper and lower clamping means, are relatively complex, which in turn makes the conventional cassettes expensive in manufacture.

Moreover, it is generally considered prudent to first remove gross debris, such as cement and impression materials in the case of dental instruments, from the instruments, and then scrub the instruments by hand, before subjecting the instruments to ultrasonic cleaning. In the use of conventional instrument cassettes, it is therefore necessary for an operator to manually handle each individual instrument in order to remove gross debris and then scrub it, before placing the instrument into the cassette. This is a relatively time consuming process and increases the possibility of the operator sustaining puncture wounds.

A further problem in the use of conventional instrument cassettes is that once the cassette containing instruments to be cleaned and sterilized is removed from an operatory in a facility having several operatories, it is not a simple matter to return that cassette to the same operatory, or to the same practitioner. Although it is known to associate source-indicating indicia with individual instruments, such indicia cannot be seen while the instrument cassette remains closed.

SUMMARY OF THE INVENTION

Accordingly, it is an object of the present invention to provide new and improved cassettes for holding medical, dental and other types of instruments through cleaning, sterilization, storage and use cycles, and new and improved methods for using such cassettes.

Another object of the present invention is to provide new and improved instrument cassettes which have a low profile configuration thereby enabling the placement of larger numbers of instrument-containing cassettes in ultrasonic cleaners and autoclaves at the same time.

Still another object of the present invention is to provide new and improved instrument cassettes which are less complicated and less expensive in construction than are conventional instrument cassettes.

A still further object of the present invention is to provide new and improved instrument cassettes and methods for using the same wherein manual removal of gross debris and hand scrubbing of the instruments can be accomplished after the instruments have been arranged and retained in the cassette so that the time for the manual cleaning step in the instrument management cycle is reduced as is the opportunity for the operator to suffer puncture wounds and the like.

Yet another object of the present invention is to provide new and improved instrument cassettes which are quickly and easily identified as coming from a particular practitioner or operatory to facilitate their return to the original source.

Briefly, these and other objects are attained by providing an instrument cassette comprising a tray member including a bottom wall in which a pattern of holes is formed to allow unimpeded fluid flow therethrough, and at least one clip member releasably securable to the tray for overlying and clamping a plurality of instruments to the tray. The at least one clip member covers only a very small area of each instrument so that the manual cleaning and scrubbing of the instruments can be accomplished after the instruments have been retained in the cassette. The construction is simple yet provides the cassette with an extremely low profile allowing a larger number of them to be stacked within an ultrasonic cleaning machine or autoclave.

In a preferred embodiment the tray member includes a pair of longitudinally extending opposed side walls and at least two instrument clamping members fixed to the bottom wall of the tray member that extend transversely substantially between the tray side walls in longitudinally spaced relationship to each other. The clip member or members are securable to the side walls of the tray member and extend substantially transversely between the side walls. The clip member or members are releasably secured to the tray member by means of resilient spring forces of spring fingers of the clip member acting on the side walls of the tray member.

BRIEF DESCRIPTION OF THE DRAWINGS

A more complete appreciation of the present invention and many of the attendant advantages thereof will be readily understood by reference to the following detailed description when considered in connection with the accompanying drawings in which:

FIG. 2 is a plan view of the instrument cassette illustrated in FIG. 1 showing the clip members secured to the tray member overlying and clamping the dental instruments to the tray member;

FIG. 3 is a section view taken along line 3—3 of FIG. 2;

FIG. 4 is a section view taken along line 4—4 of FIG. 2; and

FIG. 5 is a front elevation view of a plurality of instrument cassettes stacked one over the other for insertion into a schematically illustrated ultrasonic cleaner, autoclave, or similar device.

DESCRIPTION OF THE PREFERRED EMBODIMENTS

Figure 1:
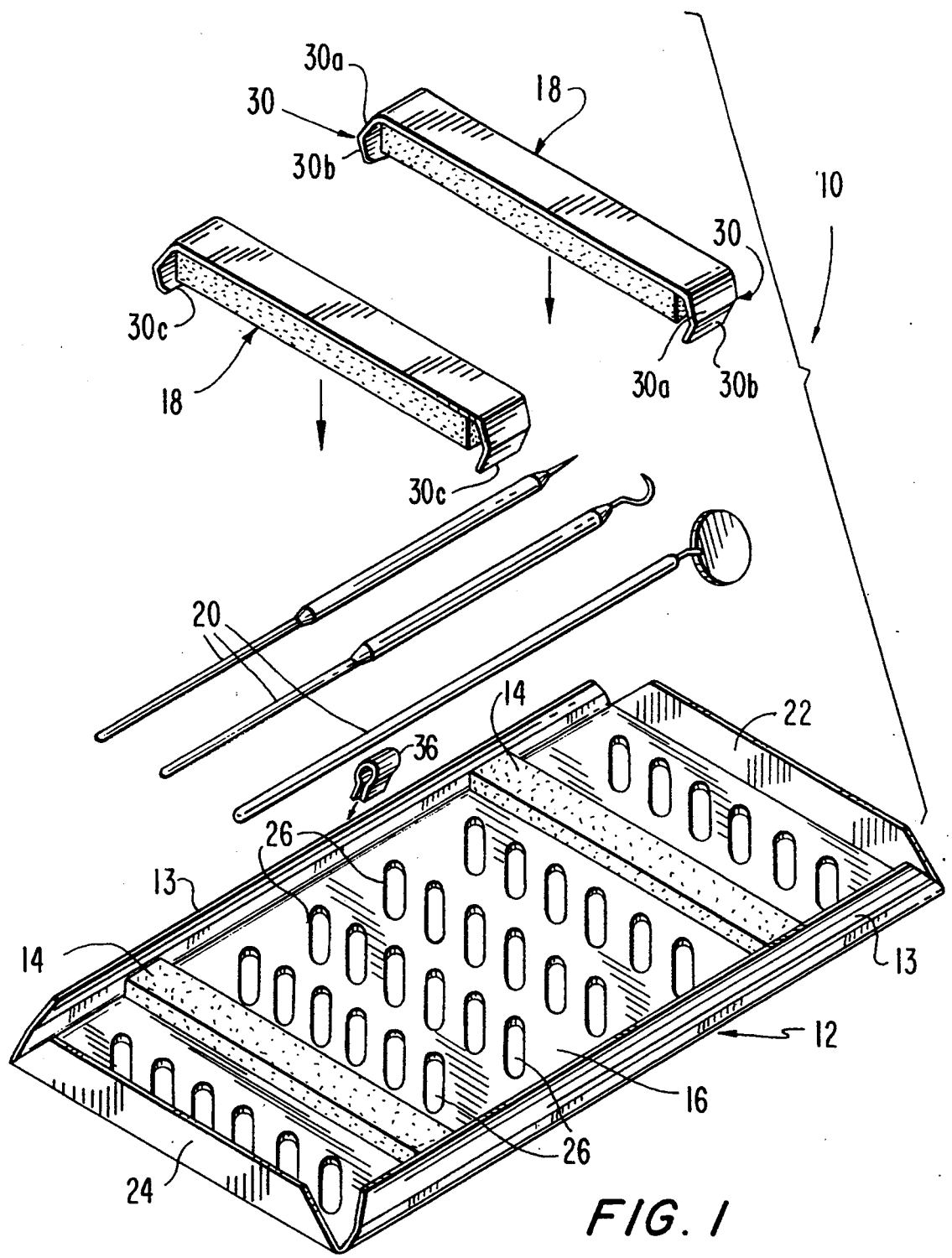
FIG. 1 is a perspective view of an instrument cassette in accordance with the invention prior to securing the clip members to the tray member and showing dental instruments in position to be retained therein.

Referring now to the drawings wherein like reference characters designate identical or corresponding parts throughout the several views, and more particularly to FIGS. 1-4, an instrument cassette in accordance with the invention, generally designated 10, comprises a substantially rectangular tray member 12 having a pair of parallel, longitudinally extending opposed side walls 13, at least two instrument clamping members 14 fixed to the bottom wall 16 of tray member 12, and a pair of clip members 18 removably securable to the tray member so as to extend substantially transversely between the tray side walls 13 to overlie and clamp the instruments 20 against the tray clamping members 14. As best seen in FIG. 2, the clip members 18 cover only a small part of each of the instruments so that the instruments remain substantially exposed while at the same time being securely retained in the cassette 10.

Tray member 12 is formed of stainless steel sheet material or the like and includes front and rear walls 22 and 24 in addition to side walls 13. A pattern of elongated holes 26 are formed in the bottom wall 16 of tray member 12 to allow unimpeded passage of ultrasonic solution.

The tray clamping members 14 each comprise an elongate pad or cushion of flexible, compressible, heat-resistant material, such as silicone rubber, and are affixed to the bottom wall 16 of tray member 12 by heat-resistant glue in a mutually spaced relationship. Each clamping member 14 extends transversely across the bottom wall 16 of tray member 12 from one side wall 13 to the other. The longitudinal spacing between the clamping members 14 is somewhat less than the length of the shortest instrument 20 to be retained within cassette 10.

Referring to FIG. 4, each of the clip members 18 has a substantially inverted U-shape and includes a substantially planar body portion 28 formed of stainless steel sheet material, a pair of securing legs 30 which are integral with and depend from respective ends of body portion 28, and a clip clamping member 34 comprising a pad or cushion of silicone rubber or other flexible, compressible, heat-resistant material affixed to the inner surface of clip body portion 28 by heat resistant glue. The tray side walls 13 and clip legs 30 are shaped such that when the clip member is associated with the tray member as described below, the clip legs 30 are resiliently bent inwardly through engagement with respective tray side walls 13 and thereby exert an outwardly directed spring force against the side walls 13 which extend upwardly and inwardly, thereby capturing the clip legs between the tray member side walls. In particular, each of the securing legs 30 is bow-shaped and comprises an outwardly and downwardly extending portion 30a and an inwardly and downwardly extending portion 30b which terminates at a free edge 30c. The outwardly and downwardly extending portion 30a connects to the inwardly and downwardly extending portion 30b at a bend 32. The distance between the lower edges 30c of each clip member in its unbent form is preferably at least slightly smaller than the distance between the upper edges 13a of the opposed tray side walls 13, while the distance between the outermost points of each securing leg 30 is generally greater than the distance between sidewall edges 13a.

In securing a clip member 18 to the tray member 12 after used instruments have been arranged on the tray clamping members 14, the clip member 18 is oriented transversely to the tray member 12, i.e. substantially perpendicularly to the side walls 13, so that the terminal edges 30c of the securing legs 30 are received between the free edges 13a of side walls 13. The clip member 18 is urged downwardly toward tray bottom wall 16, whereupon the lower spring portions 30b of the securing legs 30 engage the inner surfaces of the side walls 13 in turn bending the securing legs 30 resiliently inwardly. The terminal edges 30c of the securing legs 30 eventually abut against the upper surface of the tray bottom wall 16. The securing legs 30 have at this point been resiliently bent inwardly, and therefore exert a continuous outwardly directed spring force against the inwardly directed side walls 13. In this manner the clip member 13 is releaseably secured to the tray member 12.

In use, after a practitioner finishes with an instrument, it is placed in a tray member 12 so that a working portion of the instrument rests on one of the tray clamping members 14 while a mid-region of the shank of the instrument handle rests on the other one of the tray clamping members 14. When a plurality of instruments have been placed within the tray member, usually constituting a procedural set-up of instruments, the clip members 18 are releasably secured to the tray member 12 as described above so as to overlie the instruments and clamp them between the tray and clip clamping members 14 and 34. It is noted that the clip members 18 may be secured to the tray member 12 at any appropriate location along its length so long as opposed portions of side walls 13 are present. The clip members are preferably located inwardly of the tray clamping members 14 as best seen in FIG. 3. The clip members are urged toward the tray bottom wall 16 until the free edges 30c of the securing fingers engage the tray bottom wall 16. The depth of the flexible tray clamping members 14 and the clip clamping members 34 are such that both are urged tightly against local areas of the instruments as seen in FIG. 4 when the free edges 30c engage the upper surface of tray bottom wall 16 thereby securing the instruments in the cassette.

With the instruments reliably secured within the cassette 10 as described above, the cassette may be placed in a holding solution, and when convenient, the manual removal of gross debris from, and the manual scrubbing of the instruments can be accomplished. In accordance with the method of the invention, the manual scrubbing step is undertaken while the instruments are retained within the cassette. Thus, with the clips covering only localized areas of the retained instruments 20, the tray can be held by the operator in one hand while manual cleaning of the instruments is accomplished with the other. A plurality of instruments are thereby simultaneously manually cleaned reducing the time required for this step and at the same time it is no longer necessary for the operator to handle each individual instrument thereby eliminating the possibility of puncture wounds and the like.

After the instruments have been scrubbed, a plurality of trays are stacked one over the other in a basket or the like for placement into an ultrasonic cleaner. Referring to FIGS. 4 and 5, it is seen that the plane in which the body portion 28 of each clip 18 is situated lies vertically above the upper edges 13a of the side walls 13 so that when the cassettes 10 are stacked one over the other, each cassette rests on the body portions 28 of the clip members 18 of the cassette below it. A clearance c exists between the upper edges of the side walls and the bottom surface of the tray of the next upper cassette thereby providing room for more bulky instruments, such as reflective mirrors and the like. At the same time, however, the size of the clearance c is kept at a minimum to provide each cassette with a relatively low profile thereby allowing a larger number of cassettes to be stacked and placed within the ultrasonic cleaner and, subsequently, in the autoclave.

The cassette is removed from the ultrasonic cleaner upon completion of that step and placed into an autoclave or similar sterilizing apparatus. After the sterilizing cycle has been completed, the cassette is removed from the autoclave and returned to the operatory.

In accordance with another feature of the invention, a color coded identification clip 36 is preferably attached to the cassette before it is removed from the operatory. The color of a clip 36 will identify the particular operatory or practitioner to which or whom the cassette is to be returned after completion of the sterilization step. The clip 36 is preferably formed of anodized aluminum and simply comprises a U-shaped spring clip adapted to securely fit over one of the side walls 13 of the tray member 12.

Obviously, numerous modifications and variations of the present invention are possible in the light of the above teachings. For example, it is not necessary to use two clip members 18 as illustrated since a single clip member may be designed to securely retain the instruments in the tray member. The side walls 13 need not extend over the entire length of the tray member so long as opposed regions exist at locations at which the clip member is to be connected. The cassette can be designed to hold larger or smaller numbers of instruments, and may be sealed in a pouch during the sterilizing step so that the instrument-containing cassette will be maintained in a sterile condition during the storage step of the instrument management cycle. It is therefore to be understood that within the scope of the claims appended hereto, the invention may be practiced otherwise than as specifically disclosed herein.

I claim:

1. An instrument cassette, comprising:
   a tray member including a bottom wall and two longitudinally extending, opposed side walls;
   at least two tray clamping members fixed to said bottom wall of said tray member in longitudinally spaced relationship to each other for supporting respective end regions of instruments, each tray clamping member extending transversely substantially between said tray side walls; and
   at least one clip member extending substantially transversely between and releasably securable to said tray side walls for overlying and clamping said instruments against said tray clamping members with said clamped instruments remaining substantially exposed, said at least one clip member comprising an elongate body portion having a substantially planar upper surface and a pair of resilient securing legs depending from ends of said body portion,
   said pair of legs engaging respective ones of said tray side walls and constituting sole means for releasably securing said at least one clip member to said tray side walls.

2. An instrument cassette as recited in claim 1 wherein said at least one clip member further comprises a clip clamping member affixed to said body portion thereof.

3. An instrument cassette as recited in claim 2 wherein said tray clamping members and said clip clamping member comprise elongate pads of flexible, compressible, heat-resistant material.

4. An instrument cassette as recited in claim 2, wherein said clip clamping member is arranged on an inner surface of said at least one clip member such that said clip clamping member contacts the instruments and secures the instruments between said at least one clip member and said tray clamping members.

5. An instrument cassette as recited in claim 1 wherein said at least two tray side walls are substantially parallel to each other.

6. An instrument cassette as recited in claim 5 wherein each of said tran clamping members comprises an elongate member formed of flexible, compressible, heat-resistant material and extends substantially perpendicular to, and between, said tray side walls.

7. An instrument cassette as recited in claim 1 wherein said bottom wall of said tray member is substantially rectangular, including a first pair of parallel longer edges and a second pair of opposed shorter edges, wherein said opposed tray side walls extend from said longer edges of said tray bottom wall.

8. An instrument cassette as recited in claim 1 wherein said cassette comprises a pair of said clip members.

9. An instrument cassette as recited in claim 1 wherein said body portion of said at least one clip member has a substantially planar upper and lower surface, said upper surface being substantially situated in a plane vertically above end edges of said tray side walls.

10. An instrument cassette as recited in claim 1 further including means attachable to said tray for color-coding the same.

11. An instrument cassette as recited in claim 10 wherein said color coding means comprises a spring clip having a particular color, said clip being attachable to said tray member.

12. An instrument cassette as recited in claim 1, wherein said opposed side walls are directed inward toward each other and said pair of legs are provided with a complementary surface to said opposed side walls such that said pair of legs is positionable in any position substantially along the entire length of said opposed side walls.

13. An instrument cassette as recited in claim 1, wherein said pair of legs is positionable in any position substantially along the entire length of said opposed side walls.

14. An instrument cassette as recited in claim 1, wherein said pair of legs is positionable in a position between said tray clamping members.

15. A method for using an instrument cassette in conjunction with a cleaning, sterilization, storage and use cycle, comprising the steps of:
   providing instruments, arranging the instruments after use in a tray member of a coverless cassette having opposed side walls;

retaining instruments on said tray member by releasably securing a pair of legs of at least one clip member to said opposed side walls of said tray member such that said at least one clip member overlies and clamps the instruments to said tray member, said at least one clip member overlying only a localized part of each instrument so that a major part of each instrument remains exposed, said pair of legs engaging respective ones of said opposed side walls and constituting sole means for releasably securing said at least one clip member to said tray member;

hand scrubbing the instruments after the instruments have been arranged and secured between said at least one clip member and said tray member in the cassette;

placing the instrument-containing cassette in an autoclave or the like and sterilizing the instruments; and returning the instrument-containing cassette to an appropriate location.

16. A method as recited in claim 15 including the additional step of:

placing and holding the instrument-containing cassette in a holding solution; and thereafter placing said instrument-containing cassette into an autoclave.

17. A method as recited in claim 15 including the additional step of:

placing a color-coded clip onto said cassette after said instruments have been placed into said cassette.

18. A method as recited in claim 15 including the additional step of:

placing said instrument-containing cassette into an ultrasonic cleaning device and ultrasonically cleaning the instruments prior to placing said cassette in the autoclave.

19. A method as recited in claim 15 including the additional step of:

providing a plurality of apertures in said tray member for fluids to pass therethrough.

20. An instrument cassette, comprising:

a tray member including a bottom wall and two longitudinally extending, opposed side walls;

at least two tray clamping members fixed to said bottom wall of said tray member in longitudinally spaced relationship to each other for supporting respective end regions of instruments, each tray clamping member extending transversely substantially between said opposed side walls of said tray member; and at least one clip member extending substantially transversely between and releasably securable to said tray side walls for overlying and clamping said instruments against said tray clamping members with said clamped instruments remaining substantially exposed, said at least one clip member comprising an elongate body portion having a substantially planar upper surface and a pair of resilient securing legs depending from ends of said body portion, said pair of legs fictionally engaging respective ones of said tray side walls and constituting sole means for releasably securing said at least one clip member to said opposed side walls of said tray member in any position substantially along the entire length of said opposed side walls, said at least one clip member further comprising a clip clamping member affixed to said body portion thereof, said tray clamping members and said clip clamping member comprising elongate pads of flexible, compressible, heat-resistant material, said pads of said clip clamping member being arranged on an inner surface of said at least one clip member such that said clip clamping member contacts the instruments and secures the instruments between said at least one clip member and said tray clamping members.

* * * * *